United States Patent
Ergün et al.

(10) Patent No.: US 7,045,100 B2
(45) Date of Patent: May 16, 2006

(54) METHOD FOR PRODUCING FATTY ACID METHYL ESTER AND EQUIPMENT FOR REALIZING THE SAME

(75) Inventors: Nurhan Ergün, Vienna (AT); Peter Panning, Pöttsching (AT)

(73) Assignee: Energea Unwelttechnologie GmbH, Vienna (AT)

( * ) Notice: Subject to any disclaimer, the term of this patent is extended or adjusted under 35 U.S.C. 154(b) by 282 days.

(21) Appl. No.: 09/964,386

(22) Filed: Sep. 28, 2001

(65) Prior Publication Data

US 2002/0013486 A1 Jan. 31, 2002

Related U.S. Application Data

(62) Division of application No. 09/530,943, filed as application No. PCT/AT98/00284 on Nov. 23, 1998, now Pat. No. 6,440,057.

(30) Foreign Application Priority Data

| Nov. 24, 1997 | (AT) | ................................. A 1990/97 |
| Oct. 30, 1998 | (AT) | ................................. A 1807/98 |

(51) Int. Cl.
*B01J 19/24* (2006.01)
*B01J 3/00* (2006.01)

(52) U.S. Cl. ...................... 422/129; 422/211; 422/224; 422/225; 422/226; 422/242

(58) Field of Classification Search ........ 422/187–190, 422/198, 211, 212, 224, 225, 228; 554/174
See application file for complete search history.

(56) References Cited

U.S. PATENT DOCUMENTS

| 2,383,632 | A |   | 8/1945  | Trent .......................... 554/167 |
| 2,543,055 | A | * | 2/1951  | Pool et al. ................... 554/174 |
| 2,583,206 | A | * | 1/1952  | Borck et al. ................. 366/338 |
| 3,614,069 | A | * | 10/1971 | Murry ......................... 366/119 |
| 4,275,012 | A | * | 6/1981  | Kokubo et al. ............. 554/174 |
| 4,655,879 | A | * | 4/1987  | Brockmann et al. .......... 203/37 |
| 5,324,853 | A |   | 6/1994  | Jones et al. |

(Continued)

FOREIGN PATENT DOCUMENTS

AT 398777 6/1994

(Continued)

OTHER PUBLICATIONS

Manfred Pahl et al., "Einsatz und Auslegung Statischer Mischer", Chem. Ing. Tech. vol. 51, No. 5, pp. 347-364 (1979).

(Continued)

*Primary Examiner*—Hien Tran
*Assistant Examiner*—Jennifer A. Leung
(74) *Attorney, Agent, or Firm*—Greenblum & Bernstein, P.L.C.

(57) ABSTRACT

Method for producing fatty acid methyl ester, including compounding saturated and unsaturated higher fatty substances from at least one of vegetable and animal with an alkaline solution dissolved in alcohol to form a mixture. The method also includes emulsifying the mixture to reach a chemical balance state in a reaction section, wherein fats are transesterified into fatty acid methyl ester, wherein border surfaces of the mixture are enlarged by dynamic turbulence in the reaction section and the transesterification is performed under pressure, and wherein the pressure is reduced during transesterification. The method further includes after reaching a chemical balance state, separating residues from the fatty acid methyl ester in a phase separation section. Apparatus for producing fatty acid methyl ester.

22 Claims, 2 Drawing Sheets

U.S. PATENT DOCUMENTS

| | | | |
|---|---|---|---|
| 5,388,905 A * | 2/1995 | Ake et al. | 366/163.2 |
| 5,399,731 A | 3/1995 | Wimmer | 554/167 |
| 5,424,467 A * | 6/1995 | Bam et al. | 554/216 |
| 5,482,633 A * | 1/1996 | Muraldihara et al. | 210/651 |
| 5,514,820 A * | 5/1996 | Assmann et al. | 554/167 |
| 5,536,856 A | 7/1996 | Harrison et al. | |
| 5,945,529 A | 8/1999 | Corrigan et al. | |
| 6,015,440 A * | 1/2000 | Noureddini | 44/388 |

FOREIGN PATENT DOCUMENTS

| | | |
|---|---|---|
| EP | 041204 | 12/1981 |
| EP | 523767 | 1/1993 |
| EP | 0535290 | 4/1993 |
| EP | 535290 B1 * | 11/1994 |
| EP | 0706988 | 4/1996 |
| EP | 0713857 | 1/1999 |
| FR | 2560210 | 8/1985 |
| JP | 10-52634 | 2/1998 |
| WO | 90/08127 | 7/1990 |
| WO | WO91/05034 | 4/1991 |
| WO | 92/00268 | 1/1992 |
| WO | 96/40701 | 12/1996 |
| WO | 02/38529 | 5/2002 |
| WO | 03/087278 | 10/2003 |

OTHER PUBLICATIONS

H. Noureddini et al., "A Continuous Process for the Conversion of Vegetable Oils into Biodiesel", Proceeding of the Third Liquid Fuel Conference, Sep. 15-17, 1996, pp. 83-94.

Hossein Noureddini, "High Shear Mixing Reactor for Glycerolysis", Proceedings of an Alternative Energy Conference, Jul. 16-17, 1994, pp. 119-126.

Ullmanns Encyklopädie der Technischen Chemie, (1955) pp 500-503, 509 & 510.

English language abstract of EP 0 535 290, published Apr. 7, 1993.

Falbe et al., *Römpp Chemie Lexikon* , 9th Edition, p. 1343 (1990).

Noureddini, "High Shear Mixing Reactor for Glycerolysis" , *Liquid Fuels Lubricants and Additives from Biomass*, pp. 119-126 (1994).

Falbe et al., *Römpp*, 9th Edition, Georg Thieme Verlag Stuttgart-New York, pp. 1158 and 1159 (1990).

* cited by examiner

METHOD FOR PRODUCING FATTY ACID METHYL ESTER AND EQUIPMENT FOR REALIZING THE SAME

CROSS-REFERENCE TO RELATED APPLICATIONS

The present application is a divisional application of U.S. application Ser. No. 09/530,943, now U.S. Pat. No. 6,440,057, which is a National Stage Application of PCT/AT98/00284, filed Nov. 23, 1998, which was not published in English under PCT Article 21(2), the disclosures of which are expressly incorporated by reference herein in their entireties. The present application claims priority to Austrian Application No. 1990/97, filed Nov. 24, 1997 and Austrian Application No. 1807/98, filed Oct. 30, 1998.

BACKGROUND OF THE INVENTION

1. Field of the Invention

The invention relates to a method and equipment for producing fatty acid methyl ester, more particularly diesel fuel for vehicles, whereby saturated and unsaturated higher fatty substances of vegetable and/or animal origin are compounded with a potent alkaline solution, particularly a potassium solution, and dissolved in alcohol, particularly methanol, and the two components reach a chemical balance state through emulsification of the mixture in a reaction section with a phase separation section, whereby the fats are transesterified into fatty acid methyl ester, and on reaching the chemical balance state the residues such as triglycerides, glycerine, soap, non-transesterified fats, etc. are separated from the fatty acid methyl ester.

2. Discussion of Background

Such methods are known, whereby the alkaline solution compounded in alcohol is mixed in a mixing tank with the fat or oil for about 20 minutes up to 1 hour. After mixing, the mixture is left to stand. This sedimentation process takes approx. 5–8 hours. After sedimentation, the glycerine phase is removed. Then the liquid phase is again compounded with methanol potassium alkaline solution, if necessary, and the process of mixing and removal is repeated. The transesterified liquid is then neutralized with phosphoric acid, citric acid or other acids, whereby soap and the potassium salts of the acids are sedimented. In some cases, it is rinsed with water, whereby the water absorbs the soap, potassium solution, etc. This phase is also removed. Subsequently, all kinds of cleaning steps are possible. The process of stripping is also possible, whereby air flows in a counterflow to the ester in a scrubbing tower. The disadvantage of this process, which is based on a low-pressure transesterification process, is the long production time. Apart from the mixing process, long standing times are also required in the sedimentation phases. Moreover, the containers require a lot of space. The high static cost of heavy construction and foundations is a further disadvantage.

Another disadvantage of the known method is the fact that there is always more or less contamination of the fuel.

From Falbe and Regitz, RÖMPP Chemie Lexikon, 9th Edition, Vol. 2, Georg Thieme Verlag Stuttgart-New York 1990, page 1343, a method for the production of fatty acid methyl ester is known, wherein distillation is carried out after sedimentation of the glycerine solution in a separator, in order to purify and fractionate the methyl ester if required. Moreover, the reaction rate of the transesterification can be accelerated by increasing the temperature and with the help of alkaline or acid catalysts. The disadvantage of this method is the fact that the precipitation phase of the glycerine solution in the separator and even the possibility to accelerate the reaction time does not shorten the production time notably compared with the above state of the art.

Moreover, AT-PS 398 777 contains a method for the cleaning of raw vegetable oil esters, whereby the vegetable oil ester is obtained by alkaline transesterification. The transesterification takes place with methanol in excess, with the addition of potassium hydroxide as a catalyst. The raw vegetable oil ester is treated with water vapor, whereby a glycerine phase is produced, which is removed. In this process, intensive mixing is required for transesterification, and the distilled alcohol can be recycled after recovery in a distillation column.

However, other methods based on a high-pressure transesterification process are also known. Thereby, transesterification takes place in an autoclave with a relatively short reaction time. The disadvantage of such methods or equipment lies in the fact that an economic production of fatty acid methyl ester, for example for diesel fuel for vehicles, is absolutely impossible.

Moreover, the transesterification process in two steps is also known. Thereby, the yield in terms of quantity and quality is certainly higher than with transesterification in one step, but again economic efficiency is not possible due to the high plant and production costs.

SUMMARY OF THE INVENTION

The task of the invention is to create a method and equipment for the production of fatty acid methyl ester, in particular for diesel fuel for vehicles, which on the one hand avoid the disadvantages of the known methods, and on the other hand enables a rational production in an economically acceptable plant, preferably an industrial-sized plant, but is also economic in small plants.

The method according to the invention is characterized by mixture boundary surfaces which are enlarged by high or dynamic turbulence.

This invention enables for the first time the production diesel fuel such as eco-diesel or bio-diesel in ecologically optimal conditions of production while maintaining all the advantages thereof. With this invention, positive economic and ecological arguments are provided, which will stimulate a more intensive discourse on the role of renewable energy and resources.

Another surprising advantage results from the invention, namely in the field of waste management or hazardous waste disposal. With this invention, it is also possible to recycle and reuse used table oil ecologically. The use of used table oil in the method according to the invention is possible without reservations due to the high purity of the end products.

This invention makes it possible to accelerate the reaction by enlarging the boundary surfaces with dynamic processes during the transesterification. Due to high or powerful dynamic turbulence, the size of the drops in the liquid phases is effectively reduced, so that much smaller drops are produced, resulting in a much larger surface, which means that the chemical balance state is reached faster. Reaching the chemical balance state may take less than a minute. This means an enormous shortening of the production time. However, the method according to this invention is not suited for the so-called sedimentation method, since the sedimentation times would be too long due to the fine distribution of the drops.

According to a special feature of the invention, the high or powerful dynamic turbulence is produced by physical forces, for example mechanical shear forces. The advantage thereby is that the shear forces, which can certainly be created mechanically, produced much more powerful turbulence, thus increasing the number of drops and reducing the drop size.

In accordance with a further feature of the invention, the high or powerful turbulence is created by crack emulsification. The crack creates a high flow of the penetrating liquid, which turns into high turbulence or whirlpools at the end of the crack. This turbulence or whirlpools result in an enlargement of the boundary surfaces.

According to a special feature of the invention, the high or powerful dynamic turbulence is produced by dynamic emulsification, for example in a turbulator. In this case, the turbulence or whirlpools again result in enlargement of the boundary surfaces in the mixture.

In accordance with a further feature of the invention, the high or powerful turbulence is created by cavitation emulsification. With this process step, the reaction time can be shortened even further, since it takes only about 20 seconds with this optimization.

In accordance with a further feature of the invention, the large boundary surfaces are created by ultrasound. Using an ultrasound device, large boundary surfaces can also be created in the reaction section by additional division of the drops.

In accordance with a further feature of the invention, transesterification takes place under high pressure. The high pressure creates a high flow rate in the narrow sections of the reaction section, which in turn creates a high turbulence at the end of the narrow section.

In accordance with another feature of the invention, transesterification starts under high pressure, and the pressure is reduced during the transesterification. It is proven that the shorter the length of the reaction section, the greater the pressure loss. It is proven that the pressure loss benefits the enlargement of the boundary surfaces. The advantage thereby is that the pressure at the beginning of transesterification can be up to 200 bar. Naturally, this increases the dynamics of the turbulence. The pressure loss is transformed into an enlargement of the boundary surfaces and dynamics in the course of the reaction section.

In accordance with a special feature of the invention, separation of the phases of the emulsion is achieved physically. This advantageous process step allows a separation of the individual phases of the mixture, whereby the sedimentation phase known from the state of the art is no longer performed mechanically, for example in filtration units, but is replaced by rational, modem industrial methods.

In a further feature of the invention, the fatty acid methyl ester is cleaned after the separation of the emulsion phases. Basically, pure fatty acid methyl ester can be produced with this process step.

In accordance with a special feature of the invention, the separation of the emulsion phases is performed by exploiting the surface forces, in particular by means of filtration. With this method of separating the phases of the mixture, a high economic efficiency is achieved in industrial production.

In accordance with a further special feature of the invention, the phases of the emulsion are separated by multiphase filtration. Thereby, the glycerine phase is separated in the first step, and the triglycerides are separated as residue in the second step. In a third step, methanol is separated from the fatty acid methyl ester. Such a filter unit can also be designed as a cross-flow filter. With this advantageous process step, any number of steps can be performed and the desired purity achieved. Thus, the production of summer or winter diesel as eco-diesel or bio-diesel depending on the fatty acid chain is quite conceivable.

In accordance with a further feature of the invention, filters from membrane technology are used for filtration, for example in the ultra and/or nano and/or micro range. With the technology of today, such filters guarantee trouble-free operation, whereby these filters are also very easy to clean.

In accordance with a special feature of the invention, lipophilic and/or hydrophilic and/or amphoteric filters are used. The property of the filter is selected with a view to the intended purpose.

In accordance with a special feature of the invention, separation of the phases of the emulsion is achieved chemically. Such a method of separation is advantageous for the separation of phases, whereby the sedimentation times known from the state of the art can be reduced to minutes.

In accordance with a special design of the invention, multiphase distillation is performed once chemical balance state is reached, possibly after separation of the phases of the emulsion. Distillation can be performed directly on reaching chemical balance state, whereby methanol is removed at the same time. It is also conceivable that distillation be performed after filtration.

In accordance with a special feature of the invention, multiphase distillation includes at least one vacuum distillation. With this advantageous process step, a targeted separation of the individual substances is possible, whereby the temperatures at which the process is carried out can be reduced by the vacuum. Basically, pure fatty acid methyl ester can be produced with distillation.

In accordance with a special design of the invention, multiphase distillation includes at least one evaporation, in particular down-flow evaporation. With this type of evaporation, a more effective separation of the substances to be separated is achieved.

In accordance with another special design of the invention, multiphase distillation includes at least one evaporation, in particular thin-layer evaporation. This type of evaporation also permits targeted separation of the substances.

In accordance with a further feature of the invention, multiphase distillation includes fractionated condensation. With this advantageous process step, any number of steps can be performed and the desired purity achieved. Thus, the production of summer or winter diesel as eco-diesel or bio-diesel depending on the fatty acid chain is quite conceivable.

In accordance with another special feature of the invention, non-transesterified substances are separated and returned to the fats upstream from the reaction section. This increases the yield of ecological fuel obtained from the basic substance input.

The aim of the invention is realized independently by an equipment for implementation of the process. The equipment according to the invention is characterized by the fact that it includes at least one container for the fats, and at least one tank each for the potent alkaline solution and the alcohol, as well as at least one mixing vessel for compounding, and that at least the container and the mixing vessel are connected to the reaction section, and that there is a unit for separating the phases of the emulsion downstream from the reaction section. With this equipment according to the invention, it is for the first time possible to realize the process according to the invention in an efficient manner and with negligible environmental pollution. The equipment according to the invention offers the advantage that it can be built in a space-saving and thus cost-efficient manner. Construction as a major industrial plant for economic operation is possible.

In accordance with a special feature of the invention, the reaction section comprises a static mixer. With this design of the invention, high or powerful dynamic turbulence for the transesterification phase can be achieved with a simple device. This standard device has proven advantageous in use with the equipment according to the invention.

In accordance with another design of the invention, the static mixer preferably comprises a pipe filled with balls of various size and/or possibly with devices such as baffles, blades, resistors, etc. This device is easy to install and does not require much maintenance during operation. The turbulence is created primarily by the rapid flow of the mixture around the balls.

In accordance with another feature of the invention, a dynamic emulsifier is included in the reaction section. Since an emulsion is to be produced in the reaction section, i.e., a liquid with two phases maintained in suspension by Braun molecular movement, such a device is particularly suitable for reaching this objective very quickly.

In accordance with a special design of the invention, a mixed form of crack emulsifier and turbulator is included in the reaction section, for example, comprising two discs moving in relation to one another, whereby the emulsion is introduced in the middle of one of the discs. The advantage of such a device can be seen in the extremely short reaction time thus possible.

In accordance with a further design variation of the invention, a turbulator is included in the reaction section. Such a device also allows for advantageous enlargement of the boundary surface within a short time.

In accordance with a special design of the invention, a mixed form of crack emulsifier and turbulator is included in the reaction section, for example consisting of two discs moving in relation to one another, whereby the emulsion is introduced in the middle of one of the discs. The advantage of such a device can be seen in the extremely short reaction time thus possible.

In accordance with a further design variation of the invention, a cavitation emulsifier is included in the reaction section. The advantage of this device is that it achieves the shortest possible reaction time without any loss of quality or quantity.

In accordance with a further design variation of the invention, an ultrasound device is included in the reaction section. The integration of an ultrasound device has proven advantageous, since the transesterification can be accelerated specifically through large border surfaces.

In accordance with a special feature of the invention, the unit for separating the phases of the emulsion is a filtration unit. With this advantageous device, separation of the individual phases of the mixture can be achieved, whereby the sedimentation phase known from the state of the art is no longer necessary as a result of the mechanical devices. It is replaced by process steps that are performed using rational, modern and industrial equipment, plants and devices.

In accordance with another feature of the invention, a surface filter using membrane technology is used as filtration unit. Such a device permits advantageously optimal results, both in terms of quality and in terms of quantity.

In accordance with a further feature of the invention, the surface filter comprises a porous carrier and a layer applied to this carrier that acts as a membrane. With such an advantageous surface filter, the plant can be operated with maximum efficiency and making best use of energy. The surface filter can, of course, also be designed as a plate.

In accordance with a design feature of the invention, the carrier is designed as a pipe. The advantage of this design is the fact that a continuous process flow is guaranteed, even with varying inflow volumes.

In accordance with a further feature of the invention, the carrier is made of aluminium oxide, porous glass or silicates, for example. Such materials are fairly easy to process and have proven their worth in the process.

In accordance with a further feature of the invention, the layer acting as a membrane has lipophilic and/or hydrophilic and/or amphoteric properties. With the choice of these properties, it is possible to determine which phase of the mixture passes through the filter and which phase remains as residue.

In accordance with a special feature of the invention, the layer acting as a membrane is a ceramic membrane made, for example, of titanium dioxide, zirconium dioxide, silicon or silicon compounds, etc. On this layer with the cited materials, a covering layer of fatty acid methyl ester forms, which will not allow the glycerine phase to pass through, for example. A glycerine layer will not form as a covering layer on this layer of titanium dioxide or zirconium dioxide.

In accordance with one design of the invention, the layer acting as a membrane has a pore size in the nano and/or micro range, in particular with a size of 1–200 nm, or 5–200 nm. Such pore sizes can be produced with modem technology, and have delivered excellent results.

In accordance with another feature of the invention, the filtration unit is or comprises a molecular sieve filter or molecular sieve membrane. Surprisingly, the separation of non-transesterified fats from the fatty acid methyl ester is also possible with such special filters.

In accordance with a further feature of the invention, the filtration unit is designed in several phases. Depending on the desired degree of purity of the fatty acid methyl ester, several filters can be arranged in series or in parallel.

In accordance with a special feature of the invention, a distillation unit comprising at least one evaporator and one condenser is included downstream from the reaction section, or possibly downstream from the phase separation unit. This unit according to the invention also makes it possible to realize the process according to the invention in an efficient manner.

In accordance with a further feature of the invention, a down-flow evaporator is used as an evaporator. Such an evaporator has the advantage that the supplied heat can be used optimally. Evaporation in a vacuum is also possible.

In accordance with another design of the invention, a thin-layer evaporator is used as an evaporator. Evaporation in a vacuum is also possible with such an evaporator. In addition, optimal results are obtained with such a device.

In accordance with a special design of the invention, a rotary flow evaporator is used as an evaporator. Due to the centrifugal force of the rotary flow evaporator, the evaporator film is particularly thin-layered, so that the plant can be operated with maximum efficiency and making optimal use of energy.

In accordance with another feature of the invention, there is a separating unit downstream from the distillation unit. By using a separating unit, residues such as glycerine can be collected easily and the quality determined. Depending on the quality found, the further procedure is then determined.

In accordance with another feature of the invention, there is a separating unit downstream from the unit for separating the phases of the emulsion. By using a separating unit, residues such as glycerine can be collected easily and the quality determined. Depending on the quality found, the further procedure is then determined.

In accordance with a further feature of the invention, the separating unit is connected to the connecting pipe from the container for the fats to the reaction section. If the analysis of the substances in the separating unit shows that there are still non-transesterified fats, these can be transesterified again. This increases the yield.

In accordance with a special design of the invention, a pump, in particular a high-pressure pump, is used to supply the liquid to the reaction section. The integration of a high-pressure pump has proven advantageous because the turbulence for transesterification creates strong dynamics and thus a large border surface.

In accordance with a further feature of the invention, the excess methanol evaporates in a flash reactor. With this step, methanol is removed from the methyl ester.

The invention is explained in more detail based on the design variation illustrated in the figures. They show:

DETAILED DESCRIPTION

By way of introduction it is noted that in the described design variation identical parts or states are identified with the same reference numbers or names, whereby the disclosures contained in the overall description can be applied accordingly to identical parts or states with the same reference numbers or names. Furthermore, individual features of the illustrated design variant can in themselves represent independent solutions in accordance with the invention.

Figure 1:
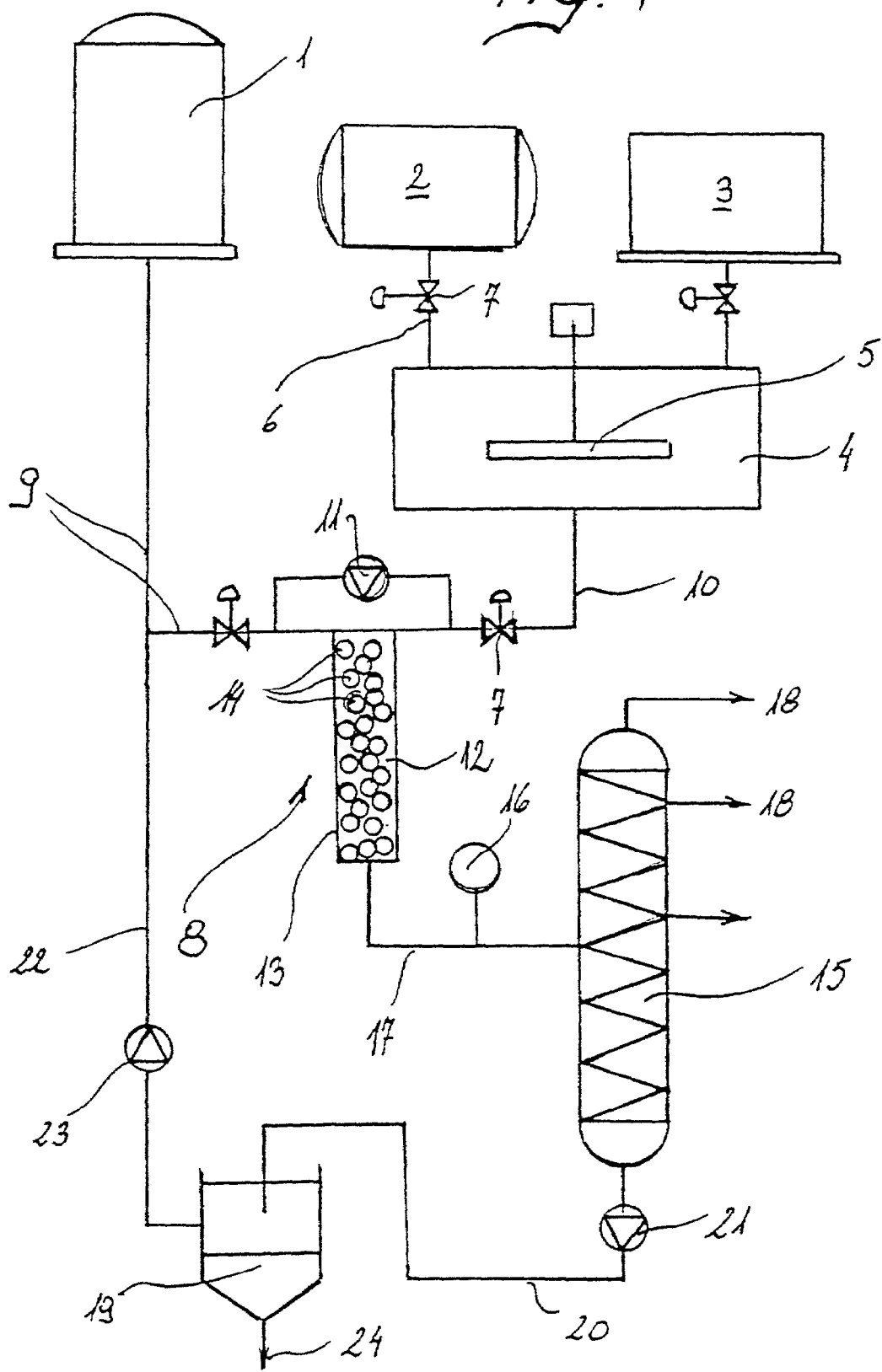
FIG. 1 is a flow chart of the process flow with a distillation unit.

In accordance with FIG. 1, container 1 contains higher saturated and unsaturated fats of vegetable and/or animal origin. A tank 2 is provided for a potent alkaline solution, particularly a potassium solution, while another tank 3 is provided for the alcohol, particularly for methanol. The alkaline solution is dissolved in the alcohol and this operation is carried out in a mixing vessel 4. For compounding the alkaline solution with the alcohol, the mixing vessel 4 is equipped with a mixer 5. The supply lines 6 to the tanks 2, 3 are fitted with control valves 7. The container 1 with the fats and the mixing vessel 4 are connected to the transesterification section 8 by connecting pipes 9 and 10. The connecting pipes 9 and 10 are equipped with additional control valves 7, and a high-pressure pump 11 is provided for introducing the fats and the solution to the transesterification section 8.

The transesterification or reaction section 8 consists of a static mixer 12, in this case made of a pipe 13 filled with balls of various sizes 14. The pipe 13 may be fitted with additional devices such as baffles, blades, etc. The static mixer 12 swirls the liquid to be transesterified from triple ester to single ester by means of high or powerful turbulence. This results in strong enlargement of the border surfaces. This is achieved by reducing the drop size of the liquid to be transesterified in the turbulence, and thus enlarging the border surface considerably. Since transesterification is a border surface reaction, the reaction rate is correspondingly increased by the enlarged surface area, so hat chemical balance state is reached very quickly.

In order to influence the reaction time even further, the process flow is carried out at specific temperatures, or it commences with high pressure that is reduced in the course of the process.

Enlargement of the border surfaces is also possible by means of ultrasound. It is therefore quite conceivable to equip the reaction section with an ultrasound device.

The liquid in chemical balance state is introduced into a distillation unit 15 via a pipeline 17. If required, a unit 16 for the removal of methanol, for example a down-flow evaporator, can be installed upstream from the distillation unit 15 in the pipeline 17.

The distillation unit 15 comprises at least one evaporator and one condenser, whereby the distillation unit 15 is designed as a vacuum distillation unit. The target substances, such as the fatty acid methyl ester, are correspondingly removed from the stages 18 of the distillation unit 15.

Of course, various forms of an evaporator can be used. For example, a down-flow evaporator, thin-layer evaporator, rotary flow evaporator, etc. can be used. In addition, the distillation unit 15 also comprises fractionated condensation. With the design of the distillation unit 15, the degree of purity of the fatty acid methyl ester can be influenced.

Non-transesterified substances are separated and collected in a separating unit 19, which is connected to the distillation unit 15 by a pipeline 20. A pump 21 is provided in the pipeline 20 for introducing these substances to the separating unit 19. These parts are analyzed in the separating unit 19 and then accordingly processed further. If necessary, part of the non-transesterified substances are returned to the fats upstream from the reaction section 8 via a pipeline 22 with a pump 23. Certain substances are removed from the separating unit 19 by a recovery unit.

Figure 2:
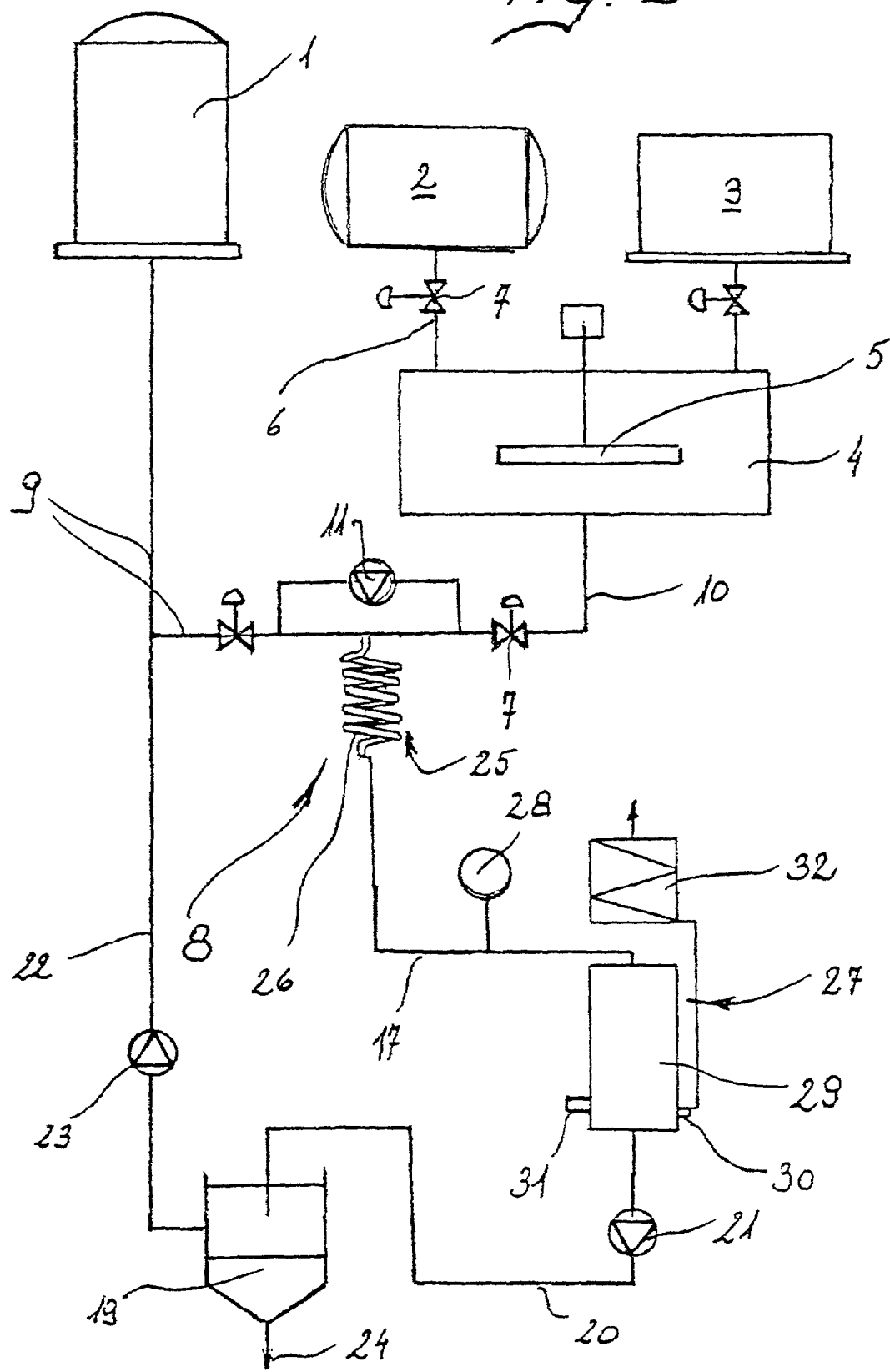
FIG. 2 is a flow chart of the process flow with a filtration unit.

In accordance with FIG. 2, container 1 again contains higher saturated and unsaturated fats of vegetable and/or animal origin. Moreover, there is again a tank 2 for a potent alkaline solution, in particular a potassium solution, and a second tank 3 for the alcohol, in particular methanol. The alkaline solution is dissolved in the alcohol and this operation is carried out in a mixing vessel 4. For compounding the alkaline solution with the alcohol, the mixing vessel 4 is equipped with a mixer 5. The supply lines 6 to the tanks 2, 3 are fitted with control valves 7. The container 1 with the fats and the mixing vessel 4 are connected to the transesterification section 8 by connecting pipes 9 and 10. The connecting pipes 9 and 10 are equipped with additional control valves 7, and a high-pressure pump 11 is provided for introducing the fats and the solution to the transesterification section 8.

The transesterification or reaction section 8 consists of a dynamic emulsifier 25, in this case made of a coiled pipe 26 filled with balls of various sizes. The pipe 26 may again be fitted with additional devices such as baffles, blades, resistors, etc. The emulsifier 25 swirls the liquid to be transesterified from triple ester to single ester by means of high or powerful turbulence. This results in strong enlargement of the border surfaces. This is achieved by reducing the drop size of the liquid to be transesterified in the turbulence, and thus enlarging the border surface considerably. Since transesterification is a border surface reaction, the reaction rate is correspondingly increased by the enlarged surface area, so that chemical balance state is reached very quickly.

Instead of the dynamic emulsifier 25, a crack emulsifier or turbulator, or a mixed form of crack emulsifier and turbulator, or even a cavitation emulsifier could be-used. Of course, it would also be conceivable to have two or more emulsifiers in series or in parallel. Enlargement of the border surfaces is also possible by means of ultrasound. It is therefore quite conceivable to equip the reaction section with an ultrasound device.

In order to influence the reaction time even further, the process flow is carried out at specific temperatures, for example 40–70° C., or it commences with high pressure that is preferably reduced in the course of the process. A temperature range in which the surplus methanol evaporates in a flash reactor and the methyl ester is thus rendered free of methanol could also be selected.

The liquid in chemical balance state is introduced into a unit 27 for separating the phases of the mixture via a pipeline 17. If required, a device 28 indicating the pressure can be introduced in the pipeline 17 upstream from the unit 27.

The unit 27 comprises at least one filtration unit 29. In accordance with the design of the unit 27, the individual phases, e.g., the fatty acid methyl ester, are separated and removed at the recovery point 30. The glycerine phase can be removed for further use at the recovery point 31.

With the design of the filtration unit 29, the degree of purity of the fatty acid methyl ester can be influenced. Of course, the fatty acid methyl ester could also be subjected to further processing in a downstream purification unit 32. It is also conceivable that the filtration unit 29 is equipped with a molecular sieve filter.

The filtration unit 29 is a surface filter manufactured using membrane technology and comprising a porous carrier, for example of aluminum oxide, preferably designed as a pipe, and a layer applied to the carrier, for example a layer of titanium dioxide. The layer can have amphoteric properties, whereby the pore size is in the nano range.

Non-transesterified substances are separated and collected in a separating unit 19, which is connected to the distillation unit 15 by a pipeline 20. A pump 21 is provided in the pipeline 20 for introducing these substances to the separating unit 19. These parts are analyzed in the separating unit 19 and then accordingly processed further. If necessary, part of the non-transesterified substances are returned to the fats upstream from the reaction section 8 via a pipeline 22 with a pump 23. Certain substances are removed from the separating unit 19 by a recovery unit.

In conclusion, it must be pointed out that for better legibility the individual components and component assemblies are not shown proportionally or to scale in the figures.

Individual features of the design example can also be the subject of independent inventions, either alone or in combination with other features. In particular, the individual designs illustrated in the figures can be the subject of independent solutions in accordance with the invention. The relevant functions and solutions can be found in the detailed descriptions of these figures.

What is claimed:

1. An apparatus for producing fatty acid methyl ester, comprising:
    at least one container for fats;
    a tank for alkaline solution;
    a tank for alcohol;
    a mixing vessel for compounding the alkaline solution and the alcohol;
    a reaction section connected to the at least one container and the mixing vessel through a high pressure pump capable of achieving a pressure of 200 bar for introducing the fats, the alkaline solution and the alcohol to the reaction section, said reaction section being structured and arranged to perform transesterification under pressure with the pressure being reduced during transesterification, said reaction section comprising a static mixer comprising a pipe filled with balls to enlarge boundary surfaces of the mixture of fats, alkaline solution and alcohol in said reaction section; and
    a separation unit downstream from the reaction section.

2. The apparatus of claim 1, wherein the separation unit comprises a filtration unit.

3. The apparatus of claim 2, wherein the filtration unit comprises a surface filter comprising a membrane.

4. The apparatus of claim 3, wherein the surface filter comprises a porous carrier and a layer applied to the porous carrier, which layer acts as a membrane.

5. The apparatus of claim 4, wherein the porous carrier comprises a pipe.

6. The apparatus of claim 4, wherein the porous carrier comprises one of aluminum oxide, porous glass, and silicate.

7. The apparatus of claim 4, wherein the layer acting as a membrane has at least one of lipophilic, hydrophilic, and amphoteric properties.

8. The apparatus of claim 4, wherein the layer acting as a membrane comprises a ceramic membrane.

9. The apparatus of claim 8, wherein the ceramic membrane comprises one of titanium dioxide and zirconium dioxide.

10. The apparatus of claim 4, wherein the layer acting as a membrane has a pore size which is at least one of a nano pore size and a micro pore size.

11. The apparatus of claim 10, wherein the pore size is 5–200 nm.

12. The apparatus of claim 2, wherein the filtration unit comprises one of a molecular sieve filter and a molecular sieve membrane.

13. The apparatus of claim 2, wherein the filtration unit comprises a multiphase filter.

14. The apparatus of claim 1, wherein the separation unit comprises a distillation unit comprising at least one evaporator and at least one condenser.

15. The apparatus of claim 1, further comprising a distillation unit comprising at least one evaporator and at least one condenser downstream from the separation unit.

16. The apparatus of claim 1, further comprising a downflow evaporator.

17. The apparatus of claim 1, further comprising a thin-layer evaporator.

18. The apparatus of claim 1, further comprising a rotation flow evaporator.

19. The apparatus of claim 1, further comprising a distillation unit which is upstream of the separation unit.

20. The apparatus of claim 1, further comprising an additional separation unit downstream from the separation unit.

21. The apparatus of claim 20, wherein the additional separation unit is connected to the reaction section by a connecting pipe from the at least one container for the fats.

22. The apparatus of claim 1, further comprising a flash reactor downstream of the reaction section for evaporating surplus alcohol.

* * * * *